United States Patent [19]

Baker

[11] Patent Number: 4,550,370
[45] Date of Patent: Oct. 29, 1985

[54] PACEMAKER PROGRAMMER WITH TELEMETRIC FUNCTIONS

[75] Inventor: Richard W. Baker, Anoka, Minn.

[73] Assignee: Medtronic, Inc., Minneapolis, Minn.

[21] Appl. No.: 701,055

[22] Filed: Feb. 13, 1985

Related U.S. Application Data

[63] Continuation of Ser. No. 437,665, Oct. 29, 1982, abandoned.

[51] Int. Cl.$^4$ .............................................. G06F 15/42
[52] U.S. Cl. ................................... 364/413; 364/417; 128/419 P; 128/419 PG; 128/904; 128/696
[58] Field of Search ................................ 364/413, 417; 128/419 P, 419 PG, 904, 696, 700, 710

[56] References Cited

U.S. PATENT DOCUMENTS

| | | | |
|---|---|---|---|
| 3,920,005 | 11/1975 | Gombrich et al. | 128/904 |
| 4,026,305 | 5/1977 | Brownlee et al. | 128/419 PG |
| 4,232,679 | 11/1980 | Schulman | 364/413 |
| 4,241,736 | 12/1980 | Rossing et al. | 128/419 PG |
| 4,255,790 | 3/1981 | Hondeghem | 364/413 |
| 4,323,074 | 4/1982 | Nelms | 128/419 PG |

OTHER PUBLICATIONS

The Cordis Omnicor Programmable Pacing System, Cordis Corp., 1974.

*Primary Examiner*—Jerry Smith
*Assistant Examiner*—Louis Woo
*Attorney, Agent, or Firm*—John L. Rooney; Joseph F. Breimayer; Reed A. Duthler

[57] ABSTRACT

A programmer for a pacemaker which has telemetric capabilities is disclosed. The programmer, in addition to being able to program the pacemaker through telemetric transmission of programming codes can receive digital and analog (including marker) information from the pacemaker for remote display and utilization, and for program modification in response thereto, if desired. Implementation of the programmer is accomplished partly by circuitry which includes pulse duration measurement circuitry for measuring time duration intervals of incoming RF telemetric signals and partly by a firmware program stored in the programmer.

1 Claim, 8 Drawing Figures

| SPECTRAX | | XYREL | | BYREL | VERSATRAX | ENERTRAX | |
|---|---|---|---|---|---|---|---|
| 8420→23 SXT | 5984/85 SX | 5994/95 VP | 5994/95 AP | 5992 | 7000 | 7100 | NOMNL |
| PARAMETER | | RATE ppm | PW msec | SENSE mV | AMPL FULL/HALF | REFR msec | HYST bpm |
| MODE | | DMND AAI-VVI | ASYNC AOO-VOO-DOO | SYNC AAT-VVT | A-V SEQ DVI | A-V UNIV DDD | ATRIAL SYNC VDD |

| | |
|---|---|
| AUTO THLD | INHIB |
| EGM/MARKER | CALIB |
| ⬓⬓⬓ EGM | ⬓⬓⬓ EGM |
| ↔ EGM | ↔ EGM |
| PRINT ON/OFF | « PAPER |

| MEAS | READ TELEM |
|---|---|
| ENTER | REVIEW |
| TEMP | CANCEL TEMP |
| PROGRAM | |

| 1 | 2 | 3 | CLR |
|---|---|---|---|
| 4 | 5 | 6 | ■ |
| 7 | 8 | 9 | 0 |

Fig. 6

PACEMAKER PROGRAMMER WITH TELEMETRIC FUNCTIONS

This is a continuation of Ser. No. 437,665 filed on Oct. 29, 1982 now abandoned.

BACKGROUND OF THE INVENTION

1. Field of the Invention

The present invention relates to programmable cardiac pacing generators with telemetric capabilities.

2. Background of the Prior Art

Artificial cardiac pacemakers have been developed which have a large number of programmable features. For example, it has previously been possible to program the rate, the pulse width, the pulse amplitude, the refractory period, the sensitivity and the mode of operation of such pacemakers. The cardiac pacemaker could have its output inhibited and could respond to programming signals which would initiate a threshold margin test. Effects of closure of the control reed switch could be overridden, a hysteresis function could be employed, and it was also possible to provide for a high-rate limit which would exceed the normal upper rate limit of the pacemaker. Many of these programmable functions of the prior cardiac pacemakers could be programmed on the permanent or a temporary basis.

Prior programmable pulse generators further included means for signaling acceptance of a programming signal, and means to reset the program acceptance circuit if extraneous signals were detected as programming signals. The program signal acceptance circuit of the pacemaker performed several different checks on the detected programming signal including a parity check, an access code check, and a check to determine if a proper number of signals were transmitted within a given time period. Thus, it is seen that programmable cardiac pacemakers have reached a high level of sophistication.

Programming of implantable cardiac pacemakers is achieved by means of an external programming unit. Such pacemakers have RF receiving circuitry which is coupled to the transmitting-programming head of an external programming unit. The programming head of the external programming unit contained a magnet of a size which was sufficient to magnetically actuate a reed switch within the implantable cardiac pulse generator so as to close the reed switch when the programming head was properly positioned. The programming unit then programmed various functions of the cardiac pacemaker by sending a 32 binary digit (bit) word, with each bit being either a logic "1" or a logic "0" binary number. The signals generated by the programmer are typically burst of radio frequency signals at a frequency of approximately 175 KHz. For each word that is generated 33 virtually identical RF bursts of energy are applied. Pulse interval decoding is employed so that the real time separation between successive RF bursts determined whether or not these signals represent a logic "1" or a logic "0" bit.

Figure 2:
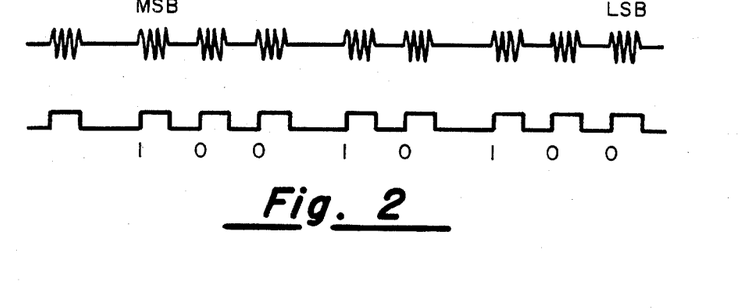
FIG. 2 shows the type of code provided for the programmer to the pulse generator.

In the programmer embodiment described herein, a relatively long time between bursts is defined as a logic "1" bit and a relatively short time is defined as a logic "0" bit. The pulse burst duration is on the order of approximately 0.35 milliseconds, the relatively long time between "1" logic bits is approximately 2.2 milliseconds and the relatively short time between "0" logic bits is approximately 1.0 milliseconds. Thus, an arbitrary series, (shown in FIG. 2) of 9 RF bursts defines a code of eight binary numbers. For the signal shown in the upper graph of FIG. 2, the binary code is "10010100". This binary number represents an octal number "224" in the conventional manner. The first number 2 of the octal number is represented by the first two most significant bits, the second number 2 of the octal number is represented by the next three bits, and the last number 4 of the octal number is represented by the last three significant bits.

The 32-bit words consist of four parts, each of which is a byte in length. These four parts are parameter code, data code, access code, and parity code and are generated in that order, least significant bit first. The first three bits of the eight-bit parameter code are not used whatsoever and are always generated as logic "0" bits. The fourth bit of the parameter code is either a logic "1" or a logic "0" bit, which respectively manifests either a temporary or permanent programming mode and the last four of the parameter bits represent the code for the particular function key that is depressed by the operator therein generating the program.

The data code pattern of the programming word consists of eight bits which define a particular value for the parameter selected.

Following the data portion of the programming word is the eight-bit access word which in the illustrated embodiment consists of the octal code "227". This word is utilized to start the process of programming the pulse generator. One purpose of the access code is to prevent extraneous signals which may be detected by a pulse generator from causing reprogramming. The final eight-bit portion of the programming word consists of an eight-bit parity code which is generated to provide proper parity based on the parameter and data portions of the word. Again, the parity portion is used as a check to prevent extraneous or undesirable programming of the pulse generator.

A number of patents have issued to assignee of the present invention which describe in detail the programmable cardiac pacemaker generally described above. These include U.S. Pat. Nos. 4,230,120, 4,233,985, 4,236,522, 4,241,736, 4,250,883, 4,253,466, 4,257,423, 4,263,915, 4,267,843, 4,273,132, 4,273,133, 4,275,738 and 4,276,883.

A programmer capable of programming the above described programmable cardiac pacemaker was developed which was capable of selecting the parameters and modes of operation of the pacing generator under the keyboard control of an operator. The construction and operation of a programmer constructed to program pacemakers constructed in accordance with the aforesaid patents is shown and described in detail in the following U.S. Pat. Nos. 4,236,524, 4,250,884, and 4,305,397.

With prior programmers of this type it is the practice to verify that the program that is transmitted to the pacemaker actually is accepted and is utilized to evoke a change in the programming of the pacemaker. To do this, skin electrodes are attached to the patient so that the skin electrodes provide artifact detection signals to the programmer. This signal consists of a program indicator pulse which has a 10% decrease in interval for one pacing cycle over the permanent rate pulses. This signal is detected by the skin electrodes, and the programmer indicates a "confirmed" message on its display. As an alternate to skin electrodes, EKG monitoring could be used with the prior programmer being constructed to pick up an artifact detection program confirmation indicating pulse. Thus, this prior programmer could provide programming signals which were inductively coupled from the programming head directly into the pacing pulse generator. However, detection of the operation of the pacing generator could only indirectly be confirmed by means of skin electrodes, or EKG, connections. Thus, while a program confirmation pulse could be received by these prior programmers through the skin electrodes, further confirmation that the correct programming change had been made by retransmission of the actual values of the parameters that were requested during the programming was not achieved in these systems.

As the battery voltage of the implanted pacemaker gradually drops, the pacemaker of the prior described patent will widen its pulse up to approximately 100% of its programmed value. In addition, the pulse rate of the threshold margin test will decrease from 100 ppm to 90 ppm, and rate hysteresis, if selected, will be inhibited. Prior to the programmer of the present invention, this rate change associated with the decrease of battery voltage could only be detected indirectly through means of skin electrodes, or EKG readings and a direct signal was not coupled from the pacing generator to the programmer to indicate battery condition.

The programmer of the present invention is constructed to function with SPECTRAX-SXT TM and ENERTRAX TM pulse generators manufactured by Medtronic, Inc., the assignee of the present invention. These pulse generators have output coils which are coupled to the programming head of the programmer, which function as transmitting coils. The programmer has receiving coils so that now the programmer can not only transmit, but can also receive telemetric information from the cardiac pacing pulse generators. The digital information that is stored in the pacing pulse generator can be transmitted in this manner includes:
(a) pulse generator model;
(b) all permanent programmable parameters and values in effect;
(c) whether the permanent pacing mode or the temporary "magnet" mode is in effect; and
(d) an elective replacement time indicator if the battery voltage is dropped to its end-of-life level (EOL). This information will appear on the programmer display and will be printed if the printer is turned on. Connection to a EKG recorder or monitor, it is not necessary to obtain this information as it is with prior programming units. The programmer of the present invention therefore has an expanded capacity for handling digital information received from the programmed pacemaker.

Immediately following a permanent or a temporary programming transmission by the programmer, the program change will enter the pulse generator memory and is automatically retransmitted to the programmer via telemetry. This telemetric digital data is received by the programmer and compared with data stored in its own memory which is related to the preceding keyboard entries. If a data match occurs, the programmer will display a "CONFIRMED" message for display and printout. An elective replacement time ditial indicator signal will also be transmitted by the pulse generator if the battery has dropped to its EOL level. The extended capabilities of the programmer and programmed pulse generator thus allow not only for the receipt of the programmed confirmation indicator pulse, but also for verification that an exact match between the requested parameters and the parameters that have actually been programmed has occurred.

Although the expanded digital capabilities of the programmer of the present invention are of great importance, perhaps of even more importance is the fact that this programmer is able to receive and utilize telemetric analog information from programmable cardiac pulse generators such as the SPECTRAX-SXT TM and ENERTRAX TM pulse generators manufactured by Medtronic, Inc. Both the SPECTRAX-SXT TM and the ENERTRAX TM pulse generators can provide an intercardiac electrogram analog transmission (EGM). The patient, at the same time, may be connected to an EKG recording system and the EKG reading and the electrogram EGM reading may be compared by a digital processing system, thereby greatly increasing the diagnostic capabilities available to the operator of the programmer.

In addition to the intercardiac electrocardiogram, the ENERTRAX TM pulse generator also transmits function marker pulses. The function marker pulses of the ENERTRAX TM pulse generator can be recorded simultaneously with the surface EKG reading to allow visual observation of pulse generator operation by denoting both atrial and ventricular events. Each marker pulse is approximately 20 milliseconds wide and has a specific amplitude and polarity, which designates the following pulse generator functions: atrial sense, unused atrial, ventricular pace, ventricular sense, and ventricular refractory sense. A 60 millisecond wide error marker pulse may also be printed whenever the programmer receives interrupted or faulty marker coding from the pulse generator which is likely to occur in the presence of strong electromagnetic interference. Because of the variable polarity and amplitude of the marker pulse, the information transmitted relating to this type of marker information is essentially analog in nature. Prior to the SPECTRAX-SXT TM and the ENTERTRAX TM pacemakers, neither transmission of electrograms or transmission of marker pulses of this type was available.

A telemetry transmission system which made possible the transmission of both analog and digital data on the same output transmission channel is disclosed in U.S. Pat. No. 4,281,664 issued Aug. 4, 1981 to Stephen R. Duggan, and assigned to Medtronic, Inc. In this patent, either analog or digital information may be selectively applied to control the frequency of a voltage-controlled oscillator. For a digital voltage of a logic "1" level, the oscillator is at one frequency, and for a digital voltage of a logic "0" level, the oscillator is at a second frequency. Analog information, on the other hand, causes the frequency of the oscillator to vary about a nominal unmodulated frequency. Bursts of energy from the voltage control oscillator are controlled by a switching circuit which insures that the rate that the bursts are sent to a ringing tank circuit is controlled in accordance with the frequency of the oscillator. As the frequency of the oscillator increases the number of bursts increases and as the frequency of the oscillator decreases, correspondingly the number of bursts decreases.

This type of transmission system, as shown in the Duggan patent, may therefore be utilized to transmit either digital information relating to pulse width, pulse rate, etc., or the analog intercardiac electrogram transmission, or alternately a marker pulse transmission. In the case of the marker pulse transmissions, the particular sensed events such as ventricular pace, atrial sense, atrial refractory sense, ventricular sense, and ventricular refractory sense are digitally encoded and are applied to D/A circuit to generate an output signal of the appropriate polarity and signal level which causes the voltage-controlled oscillator to oscillate at a particular frequency above or below its nominal output frequency, in accordance with polarity and the magnitude of the marker pulse, for a predetermined period of time. This frequency identifies which of the marker pulses is being sent and a corresponding signal is converted into an appropriate marker pulse recording on a surface EKG record. The instantaneous frequency of the voltage-controlled oscillator that corresponds to the analog value of each marker pulse is translated into a pulse duration signal for a burst of energy which is transmitted to the programmer.

DESCRIPTION OF THE DRAWINGS

The present invention is described by reference to the drawings in which.

TECHNICAL DESCRIPTION OF THE INVENTION

Figure 1:
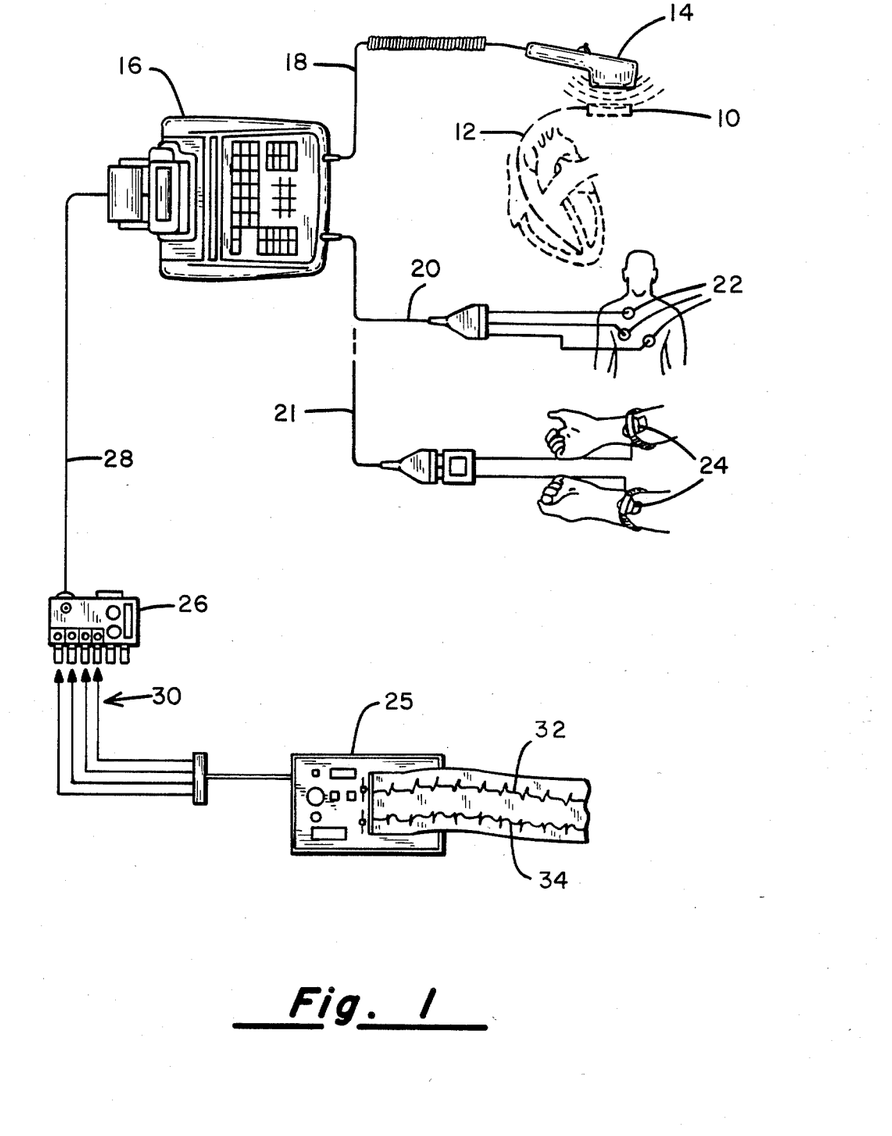
FIG. 1 shows a diagnostic illustration of the interconnections between the programmer, the EKG recorder and the patient.

The general overall system in which the programmer of the present invention is employed is shown in FIG. 1. The implanted pulse generator 10 has an intercardiac lead 12 connected to it which extends into the heart of the patient. The RF programming head 14 is positioned over the implanted pulse generator 10. The pulse generator has a reed switch (not shown) in it, and the head 14 has a magnet in it which provides a magnetic field that closes the reed switch. Upon closure of the reed switch, telemetry transmission is initiated and the telemetry functions of the pulse generator can be controlled by command transmissions from the programmer. Transmitting and receiving circuits in both the programmer and the pulse generator thus provide for a two-way communication link between the programmer and the pulse generator.

Programmed transmission signals are conducted from the programmer 16 through the cable 18 to the programming head 14 while telemetry signals from the implanted pulse generator 10 are conducted through the cable 18 into the programmer 16. The programmer 16 also may receive information on the cable 20 from the skin electrodes 22 which are attached to the patient, or from EKG wrist electrodes 24 which transmit information into the programmer on the cable 21. This general arrangement is similar to the arrangement of the prior aforementioned programming system, except for the fact that in the present invention the programmer may receive telemetered information on the cable 18. This telemetered information may be displayed on the EKG recorder 25 which is connected to the programmer 16 through the recorder adapter 26, which is coupled to the programmer by the cable 28, and to the recorder 24 by the cable 30. The recorder 25 is a two-channel recorder which allows for display of both the EGM signal 32 and the EKG signal 34 so that a physician-programmer will be able to view both displays and thereby have more information available for diagnosis.

Positioning of the programming head 14 over the implanted pulse generator 10 initiates a continuous transmission of data from the pulse generator. For the SPECTRAX-SXT TM pulse generators, this transmitted information includes an intercardiac electrograms (EGM) in the present invention which is taken from the pacing lead. ENERTRAX TM pulse generators transmit a series of marker pulses that coincide with pulse generator pacing and sensing events. These marker pulses, are amplitude-coded for specific pulse generator functions and allow for visual observation of pulse generator operations. Through keyboard command telemetry from the programmer, an ENERTRAX TM pulse generator transmission can be changed from marker pulses to an EGM signal taken from the ventricular pacing lead. The SPECTRAX-SXT TM pulse generators do not have the marker pulse telemetry function. Digital information representing the marker pulses is converted to an analog signal in the pacing generator and is supplied to control the frequency of a voltage-controlled oscillator. The repetition rate of the voltage-controlled oscillator determines the rate at which bursts of energy are transmitted from a transmission circuit, such as that shown in the aforementioned Duggan patent over the cable 18 into the programmer 16.

The programmer 16 contains a microprocessor which processes the information and converts it to digital signals which control a digital-to-analog output circuit that translates these signals into the proper marker pulses for recording. An LED may be included in the programmer to indicate when telemetry is not being received. This will occur when the programming head is not positioned over the pulse generator properly, or when telemetry is not being received because of interference.

Pressing the SPECTRAX-SXT TM or ENERTRAX TM model key on the programmer keyboard initiates an interrogation transmission by the programmer. This transmission continues until the programming head is positioned properly over the pulse generator and the communication link is achieved and verified by the programmer. The position head indicator LED will not go out until this link has been established and a response to the interrogation transmission by the pulse generator enables the programmer to test the communicication link. Adjustments necessary to "tune" the programmer to the signal characteristics of the pulse generator are automatically made at that time. Once a telemetry link has been established, the interrogation transmissions stops, and does not occur again until the SPECTRAX-SXT TM or the ENERTRAX TM model key is pressed.

Each time the SPECTRAX-SXT TM or the ENERTRAX TM model key is selected, the programming head should be positioned over the implanted pulse generator for several seconds until the position head indicator goes out. This procedure will establish a telemetry link before the programming procedure begins. To receive the EGM or marker pulse telemetry, the programming head must be positioned over the pulse generator, as described earlier, and the programmer must be connected to the EKG recorder, or other monitoring device, via the recorder-adapter. Connection of the EKG recorder to the appropriate limb lead terminals on the recorder-adapter will allow output signal selection as follows: (1) Lead I channel on the recorder corresponds to surface EKG signal detected by skin electrodes or wrist electrodes attached to the patient and connected to the programmer with the EKG cable; and (2) Lead II channel on the recorder is the surface EGM or marker pulse signal received from the pulse generator. The surface EKG and telemetered EGM/marker pulse signals are also separately coupled to two high-level output terminals on the recorder-adapter. These terminals are labeled "ECG" and "EGM/MARKER". Another terminal on the recorder-adapter provides a common ground for these two output circuits. Two control knobs on the recorder-adapter allow for separate adjustment of the high-level outputs from 0 to 1 volt.

The keyboard of the programmer of the present invention is essentially the same as the programmer described in the aforementioned patent with the exception of seven keys described below which function to control the new telemetry functions of the present programmer, which are implemented in the programmer with additional firmware storage in a programmable read-only memory. The function and the operation of the programmer when these keys are depressed is described generally below. The "READ TELEM" key when depressed and followed by the "PROGRAM" key signals the pulse generator to telemeter, that is transmit the following information: 1. The pulse generator model; 2. The current status of all programmable parameters and the pacing mode in effect; and 3. The elective replacement time indicator if battery voltage has dropped to the EOL (End-of-Life) level.

The programmer receives and processes the transmitted signal for display and printout. The READ telemetry function may be used only after the pulse generator model has been entered and before or after completion of a programming sequence. A "READ TELEM" sequence cancels any temporary program in effect except the temporary demand pacing mode in the SPECTRAX-SXT TM pulse generators and temporary pacing modes in the ENERTRAX TM pulse generators.

The "EGM/MARKER" key followed by depression of the PROGRAM key selects alternately the EGM or the MARKER telemetry function in an ENERTRAX TM pulse generator. This transmitted command to the pulse generator cancels any temporary program in effect. Positioning of the programming head over an ENERTRAX TM pulse generator initiates telemetry in the MARKER mode initially.

The "CALIB" key, when depressed during recording or monitoring of a telemetered electrogram, will cause the insertion of a 1 millivolt, 40 millisecond calibration pulse into the electrogram signal. (Due to pacemaker variation, the 1 millivolt calibration pulse may represent an actual amplitude of 0.4 millivolt to 1.6 millivolt on the telemetered EGM. However, for any one patient, the value represented by the calibration pulse will remain constant over time.) The CALIB key may be pressed any time before the calibration pulse is desired. Pressing the CALIB key during marker telemetry causes an output sequence of atrial and ventricular sense and pace markers for the purpose of calibration and identification. The marker sequence appears on the recording or on the monitor as a series of two positive pulses of decreasing amplitude and three negative pulses of increased amplitude.

Figure 4:
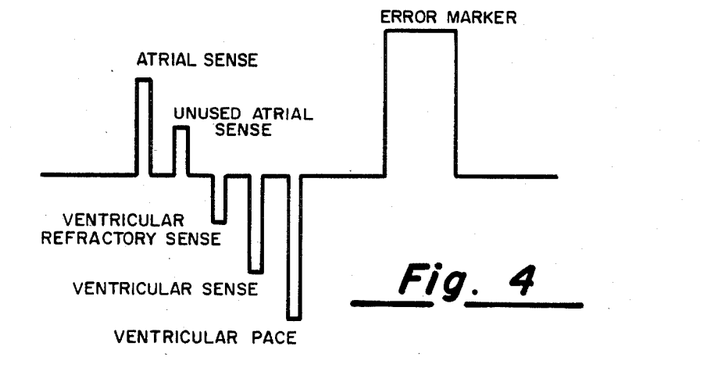
FIG. 4 is a diagrammatic showing of the marker pulses generated by the pulse generator.

The specific coding of marker pulse amplitude and polarity is shown with reference to FIG. 4. The CALIB key may also be used to aid in the adjustment of the gain and trace centering controls of an attached EKG recorder or monitor before the start of an EGM transmission. If the CALIB key is pressed before any entry of a pulse generator module, the programmer will output to the EKG recorder or monitor a series of two positive pulses of decreasing amplitude and three negative pulses of increasing amplitude. These pulses provide a convenient reference for adjusting the recording for marker controls.

The remaining four control keys required for the telemetry portion of the programmer control the amplification and bias (trace position) of the electrogram signal processed for output to a recorder or monitor as described below.

EGM (DECREASING)

This key reduces the amplitude of the EGM wave. Each time it is pressed, the signal amplitude is reduced by one-half. If the EGM signal is at its maximum amplification, the key may be pressed four times for a total reduction factor of 1/16. When minimum amplification is reached, pressing this key will have no further effect on the signal amplitude.

EGM (INCREASING)

This key increases the amplitude of the EGM waveform. Each time it is pressed, the signal amplitude is increased by a factor of 2. If the EGM signal is at its minimum level of amplification, this key may be pressed four times to increase amplitude by a factor of 16. When maximum amplitude is reached, pressing the key will have no further effect on signal amplitude. Upon initiation, EGM telemetry is always at a minimum signal amplification.

EGM (BASE-LINEDOWN)

Pressing and holding this key moves the EGM baseline down, and within limits the EGM trace will slowly shift downward while the key is depressed and stabilize when it is released.

EGM (BASE-LINEUPWARD)

This key used in conjunction with the key described above and by pressing and holding this key, the EGM trace is shifted upwardly. The combined use of these keys allows for centering of the EGM trace on the recording chart to compensate for variations in DC offset or bias holdings derived from the telemetry signal. These controls are used only after the recorder trace has been centered with the recorder centering control and the telemetry present.

Figure 3:
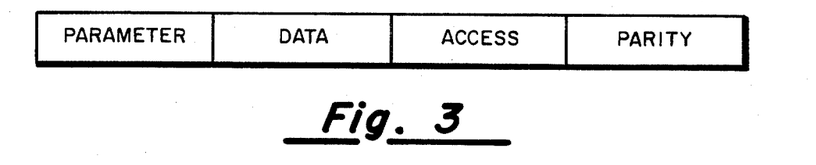
FIG. 3 shows in block format, one programming word and the various portions thereof.

The transmission of digital and analog data, including data relating to the marker pulses, is achieved by a circuit such as that shown in the Duggan U.S. Pat. No. 4,281,664. Reception of this signal by the programmer of the present invention requires that the programmer convert the pulse duration interval modulation of the incoming RF burst (FIGS. 2 and 3) into digital signals which can be processed by a microprocessor. The output of the implanted pulse generator 10 is coupled through a pulse-shaping circuit (not shown) in the Programming head 14. This pulse-shaping circuit "rounds out" the detected pulse prior to sending it to the demodulator section of the present invention. This is done to prevent the sharp, fast rising and falling edges of square pulses from radiating a group frequency spectrum from the relatively long cable. If allowed to radiate a full frequency spectrum with sufficient power, the sensitive receiver would detect this radiation within its band width and send another pulse down the cable. This pulse, of course, would interfere with respect to the desired RF pulses radiated by the implantable pulse generator.

Figure 5:
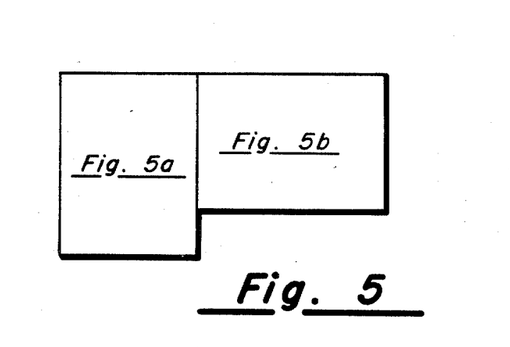
FIG. 5 shows the physical relationship of FIGS. 5a and 5b.
Figure 5A:
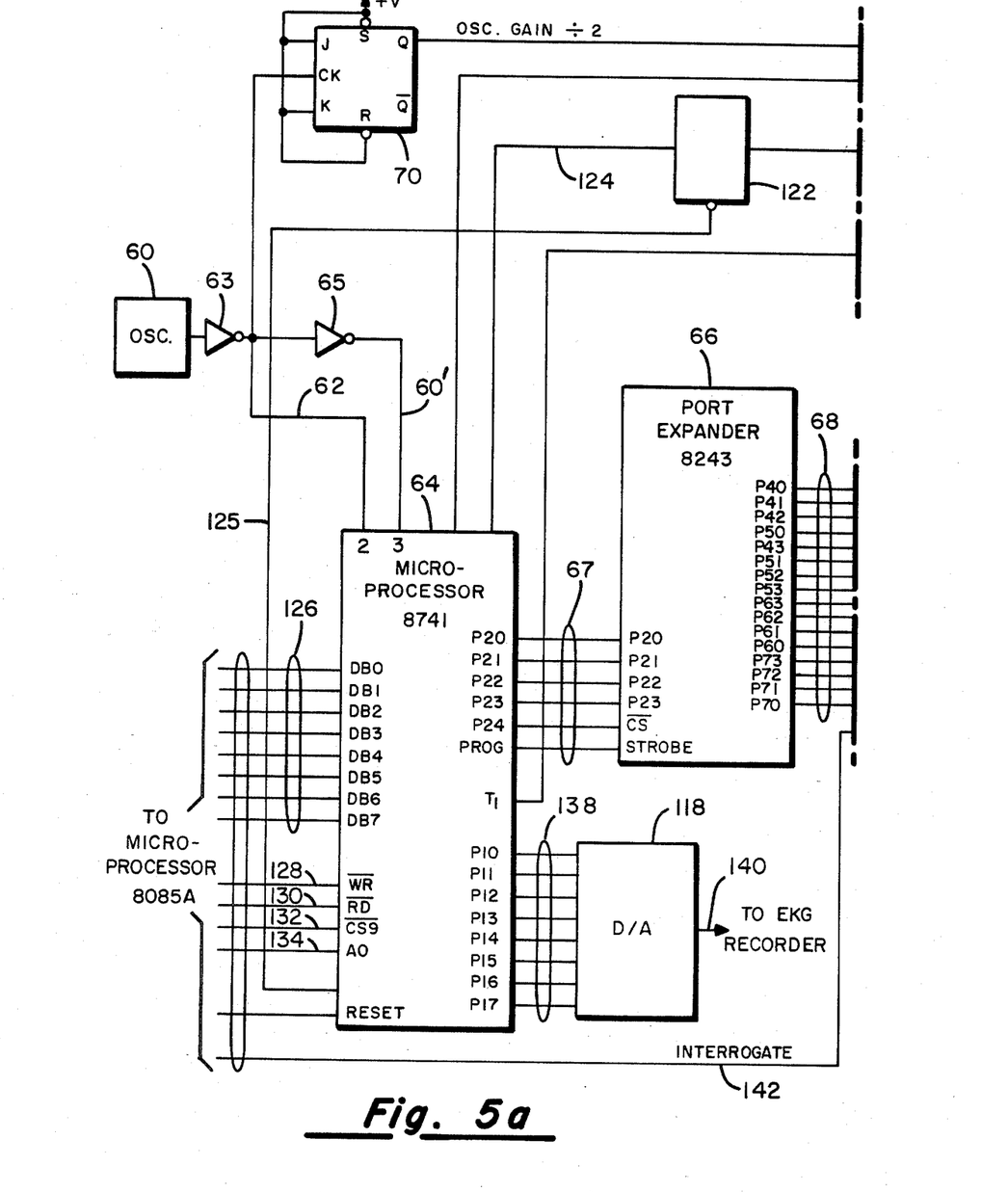
FIGS. 5a and 5b are block diagrams of the circuitry employed to implement the present invention.
Figure 5B:
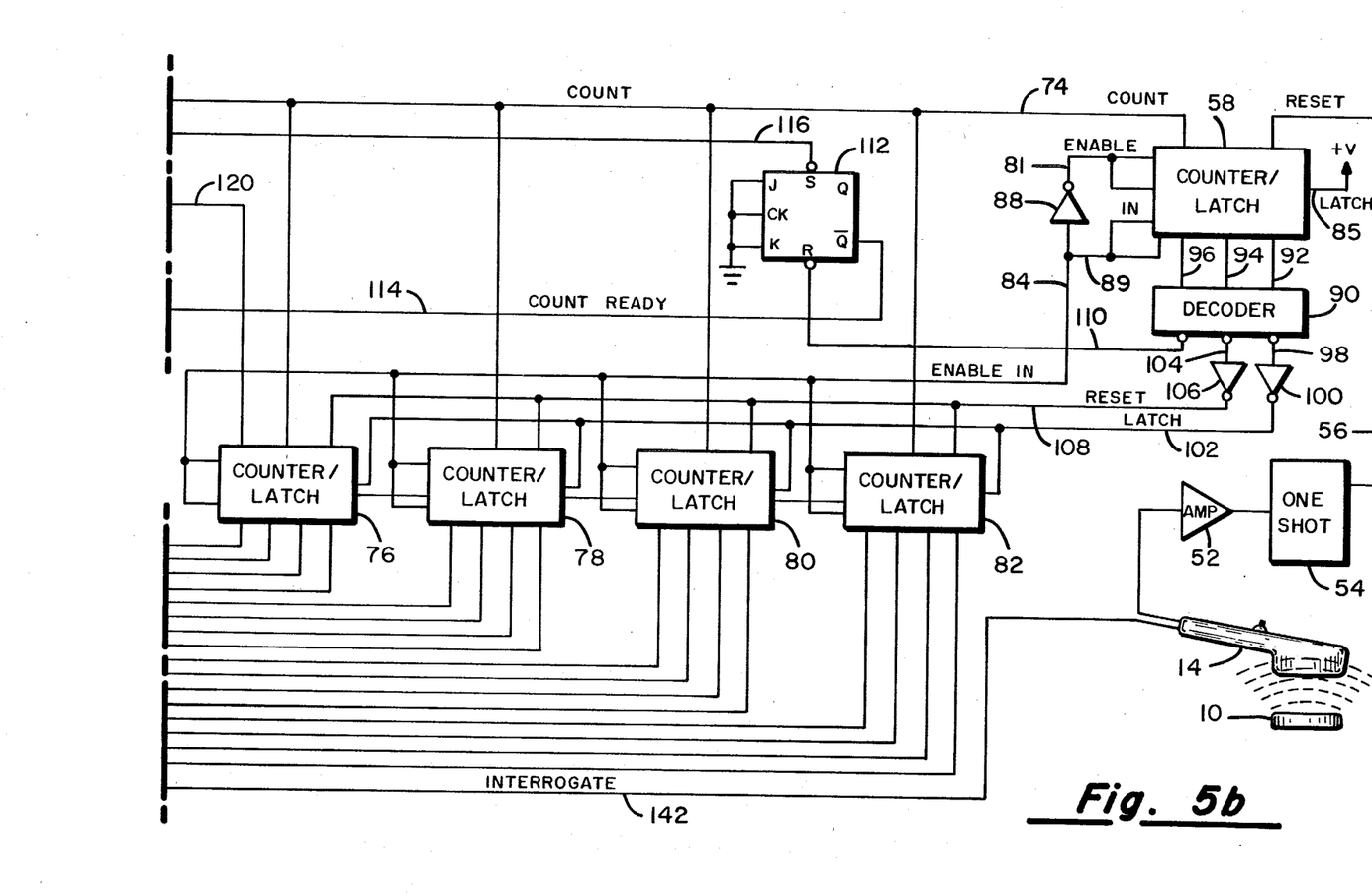
Figure 6:
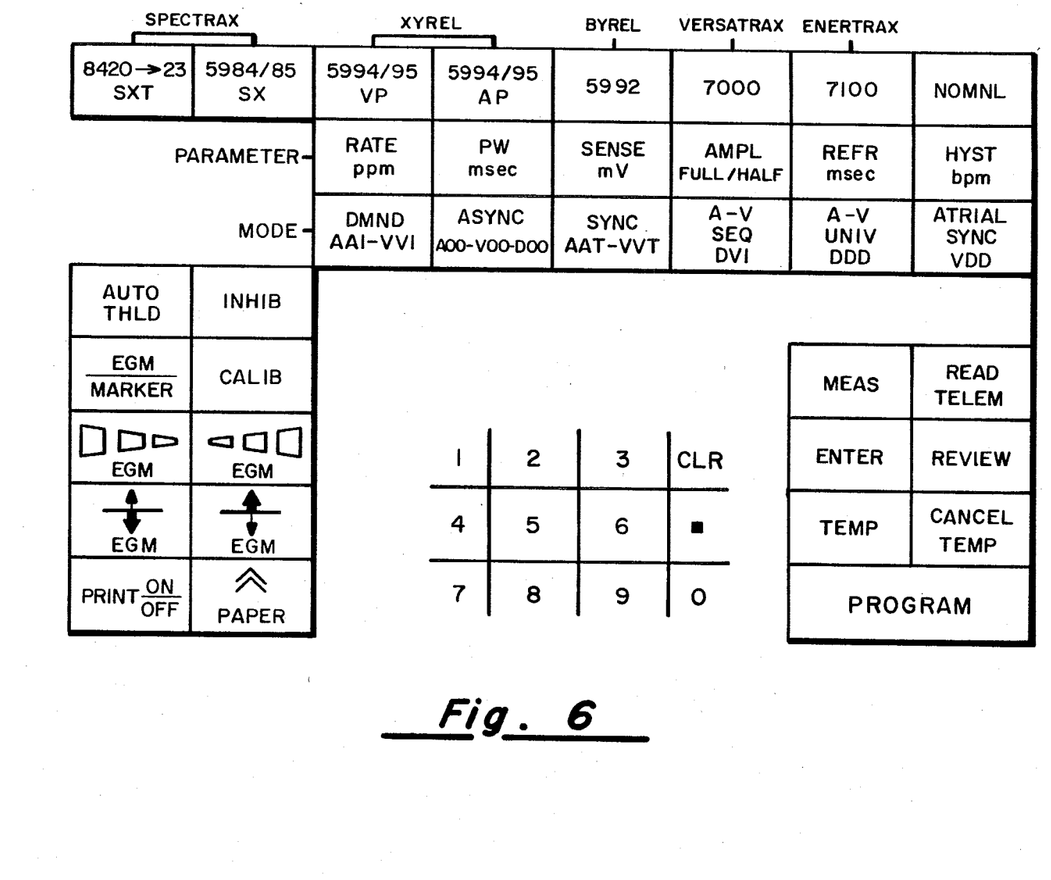
FIG. 6 is a diagrammatic showing of the keyboard of the programmer of the present invention.

The rounded pulse is amplified by the amplifier 52 which is coupled to the one-shot multivibrator 54, which provides a pulsed output signal of constant width. The one-shot 54 is used to detect the rounded pulse from the amplifier 52 at the same voltage level each time it is encountered to improve timing resolution and to reduce jitter. The one-shot 54 also shapes the pulse signal to have fast rise and fall times so these pulses may clock TTL logic circuits and its output is of a constant width. This pulse is fed on the line 56 to reset terminal of the counter 58 in order to reset the counter upon receipt of this pulse. This enables the reading portion of the circuit to start its count in order to measure the pulse interval between pulses, thereby allowing for demodulation and utilizing of the transmitted information.

The one-shot 54 takes the variable width pulses produced at the RF head and narrows them down to a repeatable and acceptable width required by the timer circuit. The received RF pulse width in the programmer head 14 depends upon how close the head is to the implanted pace generator, the field strength and how wide the pulse is for the implantable pace generator in question. The output of the one-shot should be approximately from 70 to 150 nanoseconds wide. It must be a very narrow pulse so that it does not interfere with the timer counting processes for a period longer than $\frac{1}{2}$ a clocking period.

In one embodiment of the present invention, a 3 MHz clocking rate is employed which gives a 333 nanosecond period. The crystal oscillator 60 is utilized. The system which runs at 6 MHz and is coupled on the line 62 through the inverter 63 to the input terminal 2 of the microprocessor 64 and through a second inverter 65 and the line 60' to an input terminal 3. The microprocessor 64 may be an 8741 microprocessor manufactured by Intel Corporation. The 8741 processor is a 40-pin dual in-line peripheral controller, or slave processor, which is constructed to be utilized with a master processor such as the Intel ® 8085A microprocessor. The 8741 is designated by Intel Corporation as a universal peripheral interface processor. It contains 1K bytes of program memory which may consist of either a ROM or an EPROM memory. It is an eight-bit CPU machine with a clock and a timer/counter. It utilizes ten internal address bits and an eight bit instruction bus. There are eighteen external dedicated I/O control lines. A 8243 Intel ® port expander 66 is also used in the described embodiment of the present invention. This is a sixteen bit port expander interface which expands four input lines (P-20–P-24) from the processor 64 into sixteen output lines 68. The line P-24 from the processor 64 accesses a chip selection line which is fed to the CS input of the port expander. The PROG output signal from the processor 64 is coupled to the STROBE signal input of the port expander 66. With this configuration, the PROG pin will access an address/data strobe to the port expander so that it will indicate to the port expander 66 whether data or address information is on the lines P-20–P-24. The 8741 is coupled to an 8085 microprocessor (not shown).

While the 6 MHz clocking rate is suitable for operating the slave processor 64, this clocking rate is too high to drive the additional counting circuits of the described embodiment of present invention. Also, with such high clocking rate, additional counter chips would be needed even if the chips could operate at this high speed, in order to hold the count accumulated between RF pulses. Thus, to reduce the counting rate a JK flip-flop 70 is employed to divide the clock pulse frequency by two. The flip-flop 70 supplies this signal on the line 74 as a count signal to control the counting of the counter latch 58 and the counters/latches 76–82. With a 3 MHz counting rate applied to the counters, they will be incremented every 333 nanoseconds, which establishes the resolution of the timer and indirectly the analog measurement resolution. The relationship of the time interval between RF pulses sent by the pacing generator and the manner in which that time is altered by the voltage value that is sensed at the implanted leads while the pacing generator is in the analog pacing mode, is an important consideration. For every millivolt of increase above a nominal 0 millivolt value that the leads of the pacing generator senses, the pacing generator will increase the time interval between RF pulses by approximately 3.3 microseconds. For every millivolt below the nominal 0 millivolt reading, the implantable pacing generator will decrease the RF pulse interval time by approximately 3.3 microseconds. With a timer resolution of 333 nanoseconds, this allows a resolution of the analog signal sensed on the leads to be resolved down to 0.1 millivolts.

The counters 58 and 76–82 are counters which have output latches so that the contents of these counters are transmitted to the latches, and once they are latched, these outputs remain constant independent of the contents or activities of the count registers. The transfer and latching of the count register to the output latches is controlled by a latch line 102 which transfers the count register to the output port on the falling edge of a latch enable signal. Another line 106 is utilized to reset the count register but this does not affect the latched output. An enable line 84 is also provided which must be enabled with a signal before the counter will operate.

When an RF pulse signal is received from the implanted pacemaker 10 it is transmitted through the programming head 14 and the amplifier 52 to the one-shot 54. The one-shot 54 energizes the reset line 56 of the counter 158. Prior to the energization of the reset line 56, the counter 58 will have been counting due to count pulses from the flip-flop 70 on the count line 74. When the RF pulse transmits to the one-shot 54, the contents of the counter are set to 0. The output latch line 85 of the counter 58 is held at a high state by means of a positive voltage supply. Thus, the output of the latch portion of the counter/latch 58 will continuously follow the count in the count stage. When the bit 3 of the counter 58 on the the line 84 changes from a "1" to a "0" state, it prevents the counters of 76–82 from further incrementing. This is done in order to prepare the count transfer to the output latches of these count, since the count should not change during such a transfer.

Bit 3 of the counter 58 is inverted and is supplied on the line 89 to the count terminal of the counters 76–82.

The signal on the line 84 is inverted by the inverter 88 and is supplied on the line 81 to the enable input of the counter 58 which enables the counter when it is at a logic "1" level. The pulse on the reset input line 56 that cleared the counter 58 will be in a "0" state within one-half of the 3 MHz clocking period, therefore, by the time the next clocking pulse arrives, the counter 58 will be ready to increment. Bits 0-2 of the counter 58 are sent to the inputs of a one-of-eight decoder chip 90 on the lines 92, 94, and 96 respectively. The outputs of the decoder 90 are sequenced during the following eight clocking pulses. The counter 58 counts from 0 to 8 while the decoder 90 decodes this count into series of three sequential non-overlapping pulses. The data outputs 0, 2, 4 and 6 of the decoder 90 are skipped in order to prevent overlapping sequential pulses and to allow for setup times and propagation delays in the chips which are being controlled by the sequence of pulses.

The control events which occur during the eight counting stages of the counter 58 while it counts from 0 to 8 will now be described.

Count=0. The counter 58 is reset to 0 by a detection of the RF pulse from the one-shot 54 that is applied on the line 56. The counter latches 76-82 are disabled from further incrementation in preparation for count transfer to the corresponding output latches. The counter latch 58 is enabled by the inverter 88.

Count=1. The output on the decode line 98 goes to a "0" and the inverter 100 inverts a signal and supplies a "1" on the line 102 to the latch terminal of the counters 76-82. This transfers the count then in the counter stages of the counter/latches 76-82 to the latch stages.

Count=2. The output on the line 98 now goes to a "1" driving the output of the inverter 100 to a logic "0". The counter 76-82 latch transfer is now completed.

Count=3. The output of the decoder line 104 now goes to the logic "0" level, driving the output of the inverter 106 to a logic "1" level. This signal on the line 108 resets the counters 76-82.

Count=4. The decoder output line 104 now goes to a logic "0" allowing the output of the inverter 106 to go to a logic "0" which releases the reset on the line 108.

Count=5. On this count, the line 110 will go to a "0" level which is coupled to the reset input terminal of the flip-flop 112, resetting this flip-flop.

Count=6. The count on the line 110 now goes to a "1" level completing the resetting of the flip-flop 112.

Count=7. The circuit is now idle for one clocking period and no pulses are output.

Count=8. The sequence of control events has now been accomplished and the counter 58 is now disabled. It begins to count again after the next RF pulse is detected. When the count of the counter 58 is at a count of eight, line 84 will go to a "1" level again, enabling the counters 76-82 and they will begin counting clocking pulses from this point. At the same time the counters 76-82 are enabled, the inverter 88 inverts the "1" signal on the line 84 to a logic "0" on the line 89, thus disabling the counter 58. The counter 58 is, therefore, locked up and idled with a count of eight in its counter register. The counter will remain in this state until the next RF pulse is detected which will again clear the contents of the counter 58 and the entire cycle is again repeated.

When the flip-flop 112 is reset, the $\bar{Q}$ output on the line 114 is coupled to the T1 input of the processor 64. This output signifies that the counter 58 has completed its eight counts and indicates to the processor 64 that a control cycle has just been completed, that the previous RF pulse-to-pulse time interval is latched and the latch stages of the counters/latches 76-82 may now be read. The microprocessor 64 after receiving this information will output a signal on the line 116 to the set input of the flip-flop 112 to ready it for the next cycle.

The output lines 68 of the counter/latches 76-82 are coupled to the port expander 66. These outputs are read in to the port expander under the control of the processor 64. The data in the latches portion of the counter/latches 76-82 will be available until another RF pulse is detected, at which time, the new pulse-to-pulse time interval will be transferred to these latches. Since the RF pulses are continually arriving in real time, the processor 64 has a limited time frame in which it must read in the time data, process it, and output it to either a digital-to-analog converter 118 or place it in the internal RAM (not shown) in the processor 64 for later transfer to the master processor 8085A (not shown).

The portion of the circuitry described so far allows for measurement of the incoming RF pulses intervals and for coupling the results to the microprocessor 64 or to the master processor for subsequent analysis and processing. The time interval measured by the counter/latches 76-82 is actually eight cycle counts less than the actual interval due to the time consumed by the eight-cycle control mode previously described. However, the microprocessor 64 firmware takes into account this discrepency so there is no inaccuracy.

The counters/latches 76-82 are clocked at a 3 MHz rate which allows for measurement up to approximately 23 milliseconds of time before overflow occurs on the output line 120 to the one-shot 122. The pulse-to-pulse time intervals of the implanted pacemaker all fall well within the limit of 23 milliseconds and they typically are on the order of 1 millisecond or less. If the RF head loses its telemetry link with the implanted pacing generator, either by failure of the RF head, or because of weak field strength, the RF pulses will not trigger the control cycle. Consequently, the timers and the counters/latches 76-82 will not be zeroed at regular intervals and they will overflow. The overflow which occurs on the line 120 causes the one-shot 122 to produce an output of approximately ½ second. This output is coupled on the line 124 to the input pin 38 of the processor 64.

Monitoring of the signal on line 124 will occur by the processor 64 under control of the master processor 8085A. The monitored status of the one-shot 122 is sent to the 8085A, and if it is set it indicates to the master processor that there has been a loss of telemetry link in the last ½ second. If the telemetry link is reestablished, no further counter overflows occur and the one-shot 122 will time out within ½ second and will remain with a "0" output until the next loss of telemetry. Pin 37 of the processor 64 supplies a signal on the line 125 which controls the resetting of the one-shot 122.

The digital information which is received is interpreted according to the spacing of the RF pulses as counted by the counters/latches 76-82. This interpreted data is transferred on the lines DB0-DB7 of the data bus 126 to the master processor. The control line 128 receives the "write" signal while the line 130 receives the "read" signal. The line 132 is the chip select signal line, while the line 134 indicates whether data or address information is present on the bus 126.

The digital data which can be decoded in the manner described in the aforementioned cited patents includes information on the pulse generator model, the permanent programmable parameter and values in effect, whether or not a permanent or temporary mode is in effect, and if the battery voltage has dropped to an EOL (End-Of-Life) level and a replacement time indicator. This information will be processed in the master processor. Intercardiac EGM and marker pulse information may also be processed by the microprocessor 64 since this information is dependent on the pulse-to-pulse interval of the RF pulses on the line 56 and is transmitted on the eight output lines P10–P17 through the lines 138 to the digital-to-analog converter 118. The output of the digital-to-analog converter 118 is coupled on the line 140 to an EKG recorder. The EKG recorder functions in accordance with the signals received on the line 140 to reconstruct the intercardiac electrogram or the function marker pulse signal as appropriate. Interrogation of the pacing generator is accomplished by the remote master processor on the line 142.

The initial sequence and time interval information of the RF pulse-to-pulse time interval is decoded by firmware in the processor 64. The information is decoded in digital form and it is stacked up in the internal RAM of the processor 64 and is sent to the 8085A master processor on command by the 8085. The digital-to-analog converter 118 is preferably set up for an output range of $+/-2.5$ volts and the digital input code is preferrably a complementary offset binary code (COB).

The described manner in which each detected RF pulse initiates a control mode of exactly eight counter pulses, allows for measurement of the interval between the pulses in real time with a minimum of hardwire. The processing of the information received from decoding the pulse-to-pulse interval is processed with firmware implemented in the processor 64, so that the firmware is integrally associated with hardwire to provide a unified system.

The transmission system described in the Duggan U.S. Pat. No. 4,281,664, is ideally suited to implantable cardiac pacemaker pulse generators since telemetric transmission may be achieved with this system with a minimum of energy dissipation. This is due to the fact that a short pulse is supplied to a ringing oscillatory tank circuit, and the tank circuit is not supplied with energy for the major duration of the interval between it and the beginning of the next pulse. While this system is able to conserve energy, it does present a substantial problem to the programming device which receives the transmission signal from the implanted pulse generator. This problem arises from the fact that the time interval which represents a "1" from one output pulse to the next, and the interval which represents a "0" from another output pulse to the next may vary substantially between pulse generators.

Digital data telemetry signals commence following the closure of a magnetically activated reed switch located in implantable pace generators such as the SPECTRAX-SXT TM and the ENERTRAX TM pacemakers, or following a programming sequence. Digital data is transmitted before either the analog data or the digital marker channel data is sent. Since the digital "1" and "0" time intervals vary from one pulse generator to another. These two types of pacemakers it is necessary to calibrate each individual pulse generator during the transmission of digital data. Calibration immediately after the closure of the reed switch is accomplished by the transmission of a "INTERROGATE" code from the programmer 14 in response to the signal on line 142, to the implanted pulse generator 16, immediately followed by a command from the master processor to the microprocessor 64 on the lines 126 to begin the calibration procedure. If the programming head 14 is not in a correct position to establish a telemetry link, this procedure of interrogating the pulse generator is continued until the telemetry link is established.

Because of the manner in which pulse generators are constructed the time interval variation for the "0" signals and the "1" signals is quite large, on the order of plus or minus 30% variation in time intervals. In fact, it has been found that the maximum for a "0" time interval for one pulse generator may exceed the minimum "1" time interval for another pulse generator. This overlap may be as much as 167 microseconds. On the other hand, there may be as little time as 467 microseconds between pulses in which to analyze the incoming data. Because of these overlapping time intervals predetermined "1" and "0" time interval windows are not possible to establish prior to sampling the time intervals that are sent by a particular implanted pulse generator. The time intervals between the last programming pulse and the onset of digital telemetry can be as long as 27 milliseconds.

With the SPECTRAX-SXT TM and the ENERTRAX TM pulse generators a pacing pulse can exist anywhere between the last programming pulse and the onset of digital telemetry. The leading edge and/or the falling edge of the pacing pulse therefore could be more than 21.84 milliseconds from the first data telemetry pulse. There could, therefore, be an overflow of the counters 76–82 without an actual loss of telemetry occuring during the first, second, or third time interval following the initiation of a programming sequence. However, it is possible to receive the first three RF pulses on the line 56 before it is assured that the system is in a digital data stream, assuming no noise pulses. Therefore, it is necessary to disregard the first three pulses and to ignore the overflow that might occur during the first three time intervals. The counter 76–82 is a sixteen-bit counter and the maximum count is equal to 65,535 $_{(10)}$. With a counter clocking rate of three clocking pulses for microseconds the counter is capable of registering up to 21,845 microseconds before overflowing.

The overflow bit of the counter consisting of the counter stages 76–82 is monitored by the processor 64 via the output line 120 and the one-shot 122. The overflow signal on the line 120 during the first three RF input pulses must be ignored while other overflow bit signals can be utilized to indicate a loss of telemetry. To prevent the processor 64 from waiting indefintely for the occurrence of the first three pulses to occur whenever the loss of telemetry occurs the master processor 8085A has an overriding time-out control for this situation. If the microprocessor 64 does not respond to the CALIBRATE command within a reasonable time, by loading its output buffer with an appropriate status byte, the master processor assumes a lack of telemetry lockup and proceeds accordingly. Once the first three RF pulses have occurred, following an INTERROGATE command, the slave microprocessor 64 checks the overflow bit of the counter for any loss of telemetry during the remainder of the digital data transmission. If the loss of telemetry occurs during calibration, the output buffer is loaded with another status byte at the end of the calibration cycle.

As mentioned bove the first three pulses that are supplied will be disregarded. The next sixty time intervals between pulses will be utilized for the "0" and the "1" calibration for a particular pulse generator. This is accomplished by an analysis of the time interval counts supplied to the processor 64 by the counters 76–82. After the first three pulses are discarded, the next sixty data bits from a SPECTRAX-SXT TM pacing generator will be utilized for analysis. If there is no pacing pulse prior to the data stream transmission, the first two bits of digital data are discarded and the next group of sixty data pulses will be analyzed. When an ENERTRAX TM pacing generator is used, eighty-four bits of digital data are transmitted. However, in order to keep the calibration routine the same, only sixty bits of data will be used for analysis.

The specification for the pacing generator due to the wide tolerances that are encountered for a "1" time interval is 1,000±+% microseconds, and that for a "0" level is 667±30% microseconds. The ratio of "0"/"1" time intervals must be ⅔±10%. The maximum "1" interval is 1300 microseconds, while the minimum "1" interval is 700 microseconds. The maximum "0" interval level is 867 microseconds, and the minimum of "0" interval is 467 microseconds. It is thus seen that any time interval above 1300 microseconds will be considered a lost telemetry and any time interval less than 467 microseconds will be considered a noise spike. For a given family of implanted Enertrax TM or Spectrax-SXT TM generators, the 0 to 1 time interval ratio is such that a time of "0" from one pulse generator may overlap a time interval of "1" from another pulse generator, but there is a general tracking so that as the "1" interval increases, the "0" time interval also increases. The acceptable ratio is ⅔±10%.

Prior to calibration, it is known only that the "1" and "0" time intervals will be somewhere in the range of 467 microseconds and 1300 microseconds and that the "1" time interval will be longer than the "0" time interval and that the "0" to "1" ratio is ⅔±10%. The processor 64 has a firmware program stored which is disclosed herein, which allows it to demodulate and handle the incoming data so as to supply digital data to the master processor and information to the D/A converter 118 in digital form so that the D/A converter is able to translate this information back into analog information. The programming routine which is stored in the firmware called "ZOCAL" classifies and analyzes the received time interval information. Predetermined time interval windows in the range of 450 microseconds to 1300 microseconds are established during firmware generation.

During the first phase of the "ZOCAL" routine, the time intervals from the counters 76–82 are read in and are classified as to which time window or number of windows they fit into. A table is generated from the RAM memory section which indicates how many time intervals match each window.

In the development of the firmware, substantial limitations are imposed upon the system since there are only sixty four bytes of RAM available with an 8741 processor. Because it is necessary to process sixty time interval pulses, with each piece of time data being two bytes in length, it is readily seen that the time intervals cannot be read in and stored for classification at a later time. In other words, processing must occur as the sixty time intervals are read in a "read time" mode. Since the RF bursts representing the time intervals can occur as close together as 467 microseconds, this is the maximum time period that is allowed for reading and classification of the pulse-to-pulse time intervals.

TABLE 1

|  | Bit Numbers | | | | | | | | | Address Generated | Time Range Since Counter was Cleared | | |
|---|---|---|---|---|---|---|---|---|---|---|---|---|---|
|  | 15 | 14 | 13 | 12 | 11 | 10 | 9 | 8 | 7 | | | | |
| RANGE | 0 | 0 | 0 | 0 | 0 | 0 | 0 | 0 | 0 | | 0 | μsec–45 | μsec |
|  | 0 | 0 | 0 | 0 | 0 | 0 | 0 | 0 | 1 | | 45 ⅓ | μsec–87 ⅔ | μsec |
|  | 0 | 0 | 0 | 0 | 0 | 0 | 0 | 1 | 0 | | 88 | μsec–130 ⅓ | μsec |
|  | 0 | 0 | 0 | 0 | 0 | 0 | 0 | 1 | 1 | | 130 ⅔ | μsec–173 | μsec |
|  | 0 | 0 | 0 | 0 | 0 | 0 | 1 | 0 | 0 | | 173 ⅓ | μsec–215 ⅔ | μsec |
|  | 0 | 0 | 0 | 0 | 0 | 0 | 1 | 0 | 1 | | 216 | μsec–258 ⅓ | μsec |
|  | 0 | 0 | 0 | 0 | 0 | 0 | 1 | 1 | 0 | | 258 ⅔ | μsec–301 | μsec |
|  | 0 | 0 | 0 | 0 | 0 | 0 | 1 | 1 | 1 | | 301 ⅓ | μsec–343 ⅔ | μsec |
|  | 0 | 0 | 0 | 0 | 0 | 1 | 0 | 0 | 0 | | 344 | μsec–386 ⅓ | μsec |
|  | 0 | 0 | 0 | 0 | 0 | 1 | 0 | 0 | 1 | | 386 ⅔ | μsec–429 | μsec |
|  | 0 | 0 | 0 | 0 | 0 | 1 | 0 | 1 | 0 | 32 | 429 ⅓ | μsec–471 ⅔ | μsec |
|  | 0 | 0 | 0 | 0 | 0 | 1 | 0 | 1 | 1 | 33 | 472 | μsec–514 ⅓ | μsec |
|  | 0 | 0 | 0 | 0 | 0 | 1 | 1 | 0 | 0 | 34 | 514 ⅔ | μsec–557 | μsec |
|  | 0 | 0 | 0 | 0 | 0 | 1 | 1 | 0 | 1 | 35 | 557 ⅓ | μsec–599 ⅔ | μsec |
|  | 0 | 0 | 0 | 0 | 0 | 1 | 1 | 1 | 0 | 36 | 600 | μsec–642 ⅓ | μsec |
|  | 0 | 0 | 0 | 0 | 0 | 1 | 1 | 1 | 1 | 37 | 642 ⅔ | μsec–685 | μsec |
|  | 0 | 0 | 0 | 0 | 1 | 0 | 0 | 0 | 0 | 38 | 685 ⅓ | μsec–727 ⅔ | μsec |
|  | 0 | 0 | 0 | 0 | 1 | 0 | 0 | 0 | 1 | 39 | 728 | μsec–770 ⅓ | μsec |
|  | 0 | 0 | 0 | 0 | 1 | 0 | 0 | 1 | 0 | 40 | 770 ⅔ | μsec–813 | μsec |
|  | 0 | 0 | 0 | 0 | 1 | 0 | 0 | 1 | 1 | 41 | 813 ⅓ | μsec–855 ⅔ | μsec |
|  | 0 | 0 | 0 | 0 | 1 | 0 | 1 | 0 | 0 | 42 | 856 | μsec–898 ⅓ | μsec |
|  | 0 | 0 | 0 | 0 | 1 | 0 | 1 | 0 | 1 | 43 | 898 ⅔ | μsec–941 | μsec |
|  | 0 | 0 | 0 | 0 | 1 | 0 | 1 | 1 | 0 | 44 | 941 ⅓ | μsec–983 ⅔ | μsec |
|  | 0 | 0 | 0 | 0 | 1 | 0 | 1 | 1 | 1 | 45 | 984 | μsec–1026 ⅓ | μsec |
|  | 0 | 0 | 0 | 0 | 1 | 1 | 0 | 0 | 0 | 46 | 1026 ⅔ | μsec–1069 | μsec |
|  | 0 | 0 | 0 | 0 | 1 | 1 | 0 | 0 | 1 | 47 | 1069 ⅓ | μsec–1111 ⅔ | μsec |
|  | 0 | 0 | 0 | 0 | 1 | 1 | 0 | 1 | 0 | 48 | 1112 | μsec–1154 ⅓ | μsec |
|  | 0 | 0 | 0 | 0 | 1 | 1 | 0 | 1 | 1 | 49 | 1154 ⅔ | μsec–1197 | μsec |
|  | 0 | 0 | 0 | 0 | 1 | 1 | 1 | 0 | 0 | 50 | 1197 ⅓ | μsec–1239 ⅔ | μsec |
|  | 0 | 0 | 0 | 0 | 1 | 1 | 1 | 0 | 1 | 51 | 1240 | μsec–1282 ⅓ | μsec |
|  | 0 | 0 | 0 | 0 | 1 | 1 | 1 | 1 | 0 | 52 | 1282 ⅔ | μsec–1325 | μsec |
|  | 0 | 0 | 0 | 0 | 1 | 1 | 1 | 1 | 1 | 53 | 1325 ⅓ | μsec–1367 ⅔ | μsec |
|  | 0 | 0 | 0 | 1 | 0 | 0 | 0 | 0 | 0 | | 1368 | μsec–1410 ⅓ | μsec |
|  | 0 | 0 | 0 | 1 | 0 | 0 | 0 | 0 | 1 | | 1410 ⅔ | μsec–1453 | μsec |
|  | 0 | 0 | 0 | 1 | 0 | 0 | 0 | 1 | 0 | | 1453 ⅓ | μsec–1495 ⅔ | μsec |
|  | 0 | 0 | 0 | 1 | 0 | 0 | 0 | 1 | 1 | | 1496 | μsec–1538 ⅓ | μsec |

TABLE 1-continued

| Bit Numbers | | | | | | | | Address Generated | Time Range Since Counter was Cleared | |
|---|---|---|---|---|---|---|---|---|---|---|
| 15 | 14 | 13 | 12 | 11 | 10 | 9 | 8 | 7 | | |
| 0 | 0 | 0 | 1 | 0 | 0 | 1 | 0 | 0 | 1538 | ⅔ μsec–1581 μsec |

Table 1 correlates the data bits 7–15 of the counters 76–82, with the time elapsed from the last time the count was cleared. The counts of 32–52 represents the width of the search window for the incoming data. The bits 7–11 of the counters 76–82 are employed to generate the addresses 32–52 of the RAM. This minimizes the number of operations and machine cycles that are required to classify the time intervals between RF pulses.

As previously mentioned when a pulse is detected by the recording head 14 and an output pulse is generated by the one-shot 54 on the line 56, a hardware control cycle is initiated. During this control cycle the contents of the counter 76–82 are transferred into the output latches on the counters 76–82. These counters are then reset and the status flip-flop 112 is set and read by the processor 64. The counter 58 is then disabled until the next input pulse is translated to a one-shot pulse under line 56, and clocking pulses are now also counted by the counters 76–82.

The count shown in the Table 1 shows that bits 7–15 of the counters 76–82 will remain in a "0" state for a total of 128 counts plus the initial eight counts of the counter/latch 58, for a total of 136 clocking pulses after a pulse on the line 56 first occurs. Thus, until bit 7 toggles to a "1" there will be a delay of 45⅓ microseconds. Since there are three clocking pulses per microsecond incrementing of each of the bits 7–15 of the counters 76–82 from that point on will take 128 clocking pulses or 128/3=42 2/3 microseconds. Pulse-to-pulse time interval data will not be stored until the point is reached where bits 8 and 10 are both at a logic "1". This time interval corresponds to 429¼ microseconds from the clearing of the counter.

As the count continues the corresponding RAM address 32–53 are represented as the counter counts until bit 12 first toggles. Then represents the time interval from 429⅓ microseconds to 1367⅔ microseconds. If information is received within the time period up to 429⅓ microseconds it is assumed that a noise spike has been encountered. If pulses between intervals are not received until the time interval 1367⅔ microseconds are reached, it is assumed that there has been a loss of telemetry. Although the time interval is 67⅔ microseconds above the maximum specification for the "1" time interval of the pacing generator this is an acceptable deviation in practice.

It is noted that the binary-coded decimal count of the bits 7–11 when the RAM address generated is 32 is a 10. Following decoding of the bits 7–9 the decimal 10 is subtracted from the number obtained, if the result is negative, it is known that the time interval between the received pulses is less than 429¼ microseconds. Since this time interval is less than the minimum "0" specified time interval, it is assumed that a noise spike has been encountered. If this test is passed the number 32 is added to the value that is obtained and this generates the correct RAM address. The contents of this RAM address is incremented to reflect that the time interval that was collected fits the corresponding time window represented by that particular RAM address. All sixty time intervals are thus collected and classified and processing continues until an error is detected. Utilizing this procedure, all of the time intervals will be collected and classified for the time corresponding to the RAM addresses 32–53. If any time interval of the sixty time intervals was above the maximum "1" or below a minimum "0" time interval, an error would be detected and collection of data is started over again.

When all sixty of the incoming data time intervals are analyzed, a form of a histogram is formed wherein all time intervals fall between the minimum "0" time and a maximum "1" time. Analysis of the histogram is obtained by starting at the minimum "0" window time (i.e., RAM address 32), and then incrementing through the RAM memory, while searching for the first non-0 count in the histogram that is stored in the RAM memory. The first non-0 count time window and the window following it will be the "0" time window frame. If the time window for a "0" or a "1" happens to come in right at the extreme edge of a window, the time interval from one to the next could land on either side of the window edge and therefore, the window frames are allowed to be two windows wide during analysis. Following determination of the "0" windows, a "0" count must persist for a minimum of four windows due to the specified separation of the "0" and "1" time intervals. If this criteria is not met, then an error signal occurs and the 8085A master processor receives an error code indicating that noise has occurred.

Following the check for four successive "0" count windows, searching begins again for the next non-0 count. When encountered, that window and the one following it wil be the final "1" time interval window frames. All locations following this window frame out to the end of the histogram range must contain "0" counts. If a non-0 count is encountered, an error signal will again be sent to the 8085A master processor. If this criteria of a noise spike causes any time interval to fall outside the two-window test frame interval for the "0" and the two-window test frame for the "1" signals an error code will be generated.

To summarize the "ZOCAL" routine, a command code (09H) which means a code of 9 in hexadecimal form is sent from the master 8085A processor to the 8741 slave processor 64. If all of the criteria established above are met during the collection of data and analysis of the histogram, the process 64 loads zeros into its output buffer flag register (not shown). Clearing of this register indicates that the master processor has read the register. At the same time, the FO general purpose flag is cleared. The FO flag issues a lockout signal to the master processor when the processor 64 is about to load data into the data bus register. The 8085A upon issuance of the command code runs an overall timeout check so that, if the first three input pulses are not detected as indicated above, an overflow will occur indicating that telemetry link has been broken.

If any time interval exceeds an maximum "1" time interval, the 8741 slave processor 64 will load a OFH code into the output buffer flag register to indicate a lack of telemetry link. Flag FO will be cleared and further commands will be awaited. If any time interval is shorter then the minimum "0" time interval or if the pattern of the histogram does not meet the required criteria, the processor 64 will load a code FFH into the output buffer flag register to indicate the presence of noise spikes, the flag F0 will again be cleared, and the microprocessor 64 will await further commands from the master processor.

Following the end of a successful "ZOCAL" calibration run, the register bank 1 of the process 64 which consists of registers R0–R3, will respectively contain data relating to the lower "0" time window, upper "0" time window, lower "1" time window, and the upper "1" time window. This data is then used in another routine called the "ZOREF" routine, which applies additional testing criteria for accepting the digital telemetry signal. These are: (1) the current "0" window must overlap the "0" of the first test; (2) the current "1" window must lverlap the "1" window of the first test; (3) the difference between the average of the first and second "0" time intervals and the second "0" time interval must be less than 43 microseconds; (4) the difference between the "0" time and the average of the first and second "0" times must be less than 167 microseconds; (5) the difference between the "1" time and the calculated "1" time, which is equal to 1.5 times the average first and second "0" times, must be less than 167 microseconds. The programmer will transmit digital data from the processor 64 to the master processor 8085A only if all of the above criteria are met. The criteria of the "ZOREF" routine is also applied to a second transmission of telemetry data, which is tested against the first transmission of data operated on by the "ZOCAL" routine.

A microfiche appendix is submitted with this patent application in accordance with the Manual Patent Examination Procedure 608105 which relates to the deposit of computer program listings. The microfiche appendix provides a source code which describes the firmware of the program PROM utilized by the 8741 microprocess of the present invention. This program includes the code "ZOCAL" and the "ZOREF" routines described above, as well as the routines required to implement the functions previously described with respect the keyboard. The instructions contained in the source statement which are implemented in the PROM of the 8741 microprocessor is described in the publication by Intel Corporation entitled UPI-41 TM User's Manual, which is labeled "Printed in U.S.A.-/A157/0777/30K CP." The description of the source statement contained on the microfiche fully describes the implementation of the programmer of the present invention when it is considered in combination with the described hardware portion of the device. The most important routines and subroutines of the program are also preceded by a short summary of the function of the routine or subroutine. It should be noted that the program stored in the PROM includes an "Analog" subroutine which allows the measured pulse-to-pulse time interval values that are translated into intercardiac EGM and marker pulse signals by the digital-to-analog converter 118.

The microfiche appendix is hereby incorporated by reference into this application in accordance with the provision of MPEP 608.05.

I claim:

1. A method of operating a programmer for use in telemetric programming of implantable cardiac pulse generators which produce pulse-interval-modulated output signals consisting of bursts of radio frequency energy wherein a first relatively long time interval between two bursts represents a digital logic signal of a first value and a relatively short time interval between two bursts represents a digital logic signal of a second value, said first and second time intervals being variable from pulse generator to pulse generator such that the relatively short time interval associated with one pulse generator may exceed the relatively long time interval associated with another pulse generator, wherein said pulse generator telemetrically transmits a calibration signal train comprising a predetermined number of bursts having a pattern of relatively short and relatively long time intervals therebetween to said programmer, comprising:
   (a) measuring each of said short and long time intervals between said bursts of said signal train in succession;
   (b) establishing a control interval associated with each time interval measurement which allows for the measurement of the next time interval after the previous time interval measurement has been stored;
   (c) storing each of said measurements during the associated control interval;
   (d) validating said signal train only if all of said measured time intervals are greater than a predetermined minimum time interval and are less than a predetermined maximum time interval;
   (e) determining from said measurements short and long time window intervals for the pulse generator being programmed;
   (f) verifying that said signal train is valid only if said short time window interval and said long time window interval are separated by a predetermined minimum time interval value; and,
   (g) decoding telemetric messages thereafter transmitted from said pulse generator after said signal train is both validated and verified.

* * * * *